United States Patent [19]

Hirai et al.

[11] Patent Number: 4,970,023
[45] Date of Patent: Nov. 13, 1990

[54] BIPHENYL COMPOUNDS, METHOD OF PRODUCING THE SAME AS WELL AS LIQUID CRYSTAL COMPOSITIONS AND LIGHT SWITCHING ELEMENTS EACH CONTAINING THE SAME

[75] Inventors: Toshihiro Hirai; Atsushi Yoshizawa; Isa Nishiyama; Mitsuo Fukumasa; Nobuyuki Shiratori; Akihisa Yokoyama, all of Toda, Japan

[73] Assignee: Nippon Mining Co., Ltd., Japan

[21] Appl. No.: 350,700

[22] Filed: May 9, 1989

[30] Foreign Application Priority Data

May 19, 1988 [JP] Japan .................. 63-120448

[51] Int. Cl.$^5$ ............. C09K 19/12; C07C 69/96; C07C 69/00; C07C 49/76
[52] U.S. Cl. .................. 252/299.66; 252/299.67; 252/299.01; 558/270; 560/141; 568/331
[58] Field of Search ............. 252/299.01, 299.66; 558/270; 560/741; 568/331

[56] References Cited

U.S. PATENT DOCUMENTS

| | | |
|---|---|---|
| 3,947,375 | 3/1976 | Gray et al. ............ 252/299.66 |
| 4,614,609 | 9/1986 | Inoue et al. ........... 252/299.66 |
| 4,732,699 | 3/1988 | Higuchi et al. ........ 252/299.66 |
| 4,818,432 | 4/1989 | Miyazawa et al. ..... 252/299.66 |
| 4,834,907 | 5/1989 | Inoue et al. ........... 252/299.66 |
| 4,874,545 | 10/1989 | Heppke et al. ....... 252/299.66 X |
| 4,876,026 | 10/1989 | Saito et al. ........... 252/299.66 X |
| 4,886,623 | 12/1989 | Mitsuhashi et al. ... 252/299.01 X |
| 4,911,861 | 3/1990 | Higuchi et al. ....... 252/299.66 X |
| 4,918,213 | 4/1990 | Nohira et al. ........ 558/271 |

FOREIGN PATENT DOCUMENTS

| | | | |
|---|---|---|---|
| 310403 | 4/1959 | European Pat. Off. . | |
| 228703 | 7/1987 | European Pat. Off. | 252/299.66 |
| 315193 | 5/1989 | European Pat. Off. | 252/299.66 |
| 07518 | 10/1988 | PCT Int'l Appl. | 252/299.64 |
| 2199826 | 7/1988 | United Kingdom . | |

OTHER PUBLICATIONS

Nishiyama, I. et al., Jpn. Jnl. Appl. Phys. Part 2 28 (10), L 1851, 1989.

Demus et al., (ed), Flussige Kristalle in Tabellen Ill., p. 270 (1984).

*Primary Examiner*—John S. Maples
*Assistant Examiner*—Richard Treanor
*Attorney, Agent, or Firm*—Arnold, White & Durkee

[57] ABSTRACT

This invention provides novel biphenyl compounds represented by the following general formula (I):

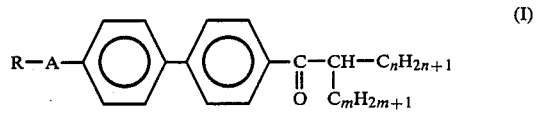

(I)

(wherein R is an alkyl group, A is selected from the single bond, —COO—, —OCO—, —OCOO— and —CO—, and each of m and n is an integer of 1 or more, provided m<n), optically active bodies thereof, liquid crystal compositions containing at least one of these compounds, light switching elements comprising at least one of the above compounds as a constituent element, and a method of producing the compound.

5 Claims, 2 Drawing Sheets

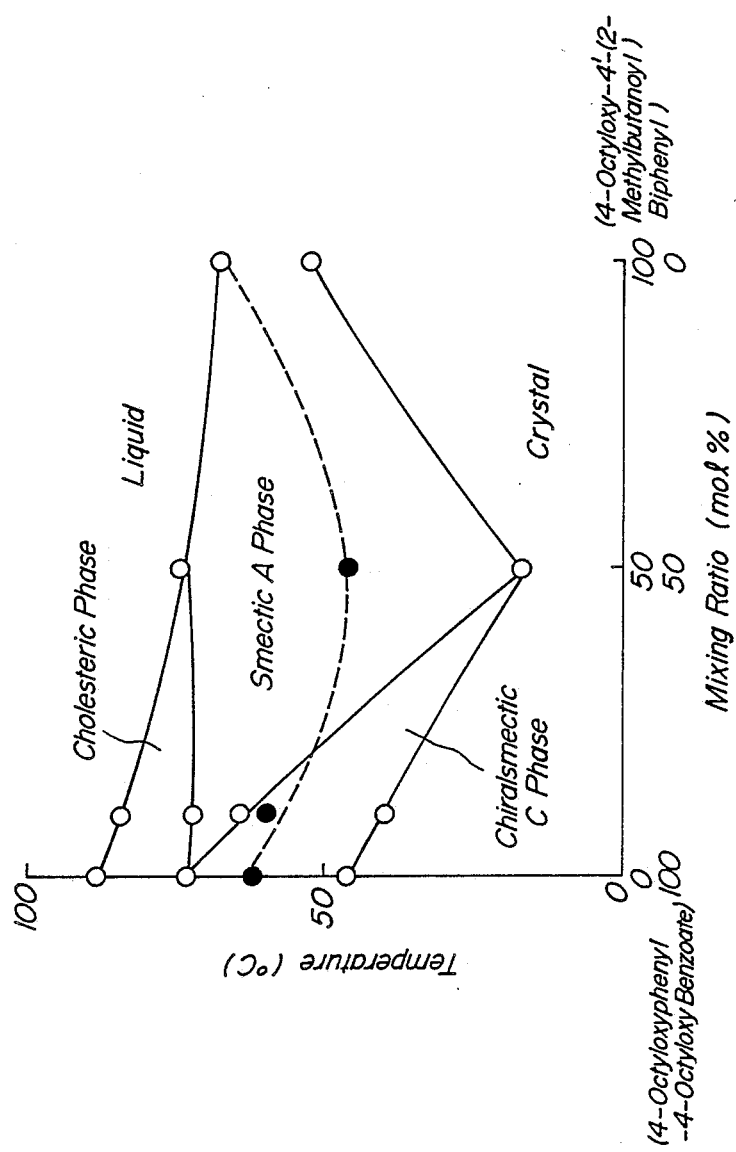

BIPHENYL COMPOUNDS, METHOD OF PRODUCING THE SAME AS WELL AS LIQUID CRYSTAL COMPOSITIONS AND LIGHT SWITCHING ELEMENTS EACH CONTAINING THE SAME

BACKGROUND OF THE INVENTION

1. Field of the Invention

This invention relates to novel biphenyl compounds which can have a stable thermotropic liquid crystal state and can be utilized as a liquid crystalline material for use in optoelectronics related elements using a liquid crystal and electrochemichromism such as a display for a liquid crystal television receiver, optical printer head, opto-Fourier transform element, light valve and the like as well as liquid crystal compositions containing the above compound and light switching elements using the above compound as a constituent element.

2. Related Art Statement

Liquid crystalline compounds having asymmetric carbon in their molecule can have a chiral smectic C phase in the liquid crystal structure and may exhibit properties as a ferroelectric liquid crystal having a fast response rate, so that they are recently expected as a liquid crystalline material for displaying means requiring a high speed response characteristics. Such a material is required to have properties such a large spontaneous polarization low viscosity the chiral smectic C phase exhibited over a wide temperature range inclusive of room temperature, and the like. However, materials sufficiently satisfying these properties are not yet provided at present.

Particularly, in the case of noticing the fast response characteristics it is preferable to achieve large spontaneous polarization. In this connection, the inventors have previously found that compounds having an asymmetric carbon at an α-position and ketone group directly bonded to a benzene ring in the molecule are stable against light or the like and wide in the temperature range enantiotropically forming a liquid crystal state. Particularly when optical activity is given to the asymmetric carbon, they become a ferroelectric liquid crystal having a large spontaneous polarization (International Publication No. WO88/07518).

On the other hand, in the case of noticing the low viscosity, the use of biphenyl as a nucelus portion of the liquid crystal is known to be promising. In this connection, there has been proposed a biphenyl compound fepresented by the following formula:

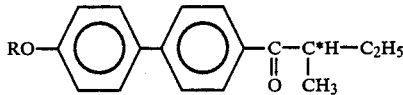

(wherein R is a straight or branched alkyl group having a carbon number of 1 to 18) as a compound having an asymmetric carbon at the α-position and a ketone group directly bonded to biphenyl ring (Japanese Patent laid open No. 60-13729).

However, there is no example for the synthesis of such a biphenyl compound, and also the properties of this biphenyl compound are not clarified at all. Further, the bonding between R and the biphenyl group in the above formula is restricted to only a bond through —O—. However, various changes of the properties can generally be expected by changing a connecting group.

SUMMARY OF THE INVENTION

The inventors have previously found that compound having an asymmetric carbon at an α-position and a ketone group directly bonded to a benzene ring become a compound having a large spontaneous polarization by giving an optical activity to the asymmetric carbon as mentioned above. With the foregoing in mind, the inventors have made further studies assuming that when a biphenyl having an asymmetric carbon at an α-position and a ketone group directly bonded to biphenyl ring is used as a skeleton of a liquid crystalline compound, the resulting compound displays a ferroelectricity and fast response characteristics. The inventors have further found that novel biphenyl compounds can be provided by changing a connecting group between an alkyl chain oppositely bonded to the ketone group and the biphenyl ring.

The invention is based on the above knowledge and provides novel biphenyl compounds useful as a liquid crystal composition as well as liquid crystal compositions containing these compounds.

It is another object of the invention to provide liquid crystal displaying elements having fast response characteristics by using the above novel biphenyl compound or the liquid crystal composition containing the same.

That is, the invention provides a novel biphenyl compound represented by the following general formula (I):

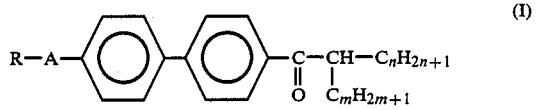

wherein R is an alkyl group, A is selected from a single bond, —COO—, —OCO—, —OCOO— and —CO— and each of m and n is an integer of 1 or more provided $m < n$, as well as a liquid crystal composition containing the above compound and a light switching element using the above compound as a constituent element.

BRIEF DESCRIPTION OF THE DRAWINGS

The invention will be described with reference to the accompanying drawings, wherein:

FIG. 2 is a phase diagram when 4-octyloxy-4'-(2-methylbutanoyl) biphenyl disclosed in Japanese Patent laid open No. 60-13729 is mixed with a well-known compound of 4-octyloxyphenyl-4-octyloxy benzoate at various mixing ratios.

DESCRIPTION OF THE PREFERRED EMBODIMENTS

Figure 1:
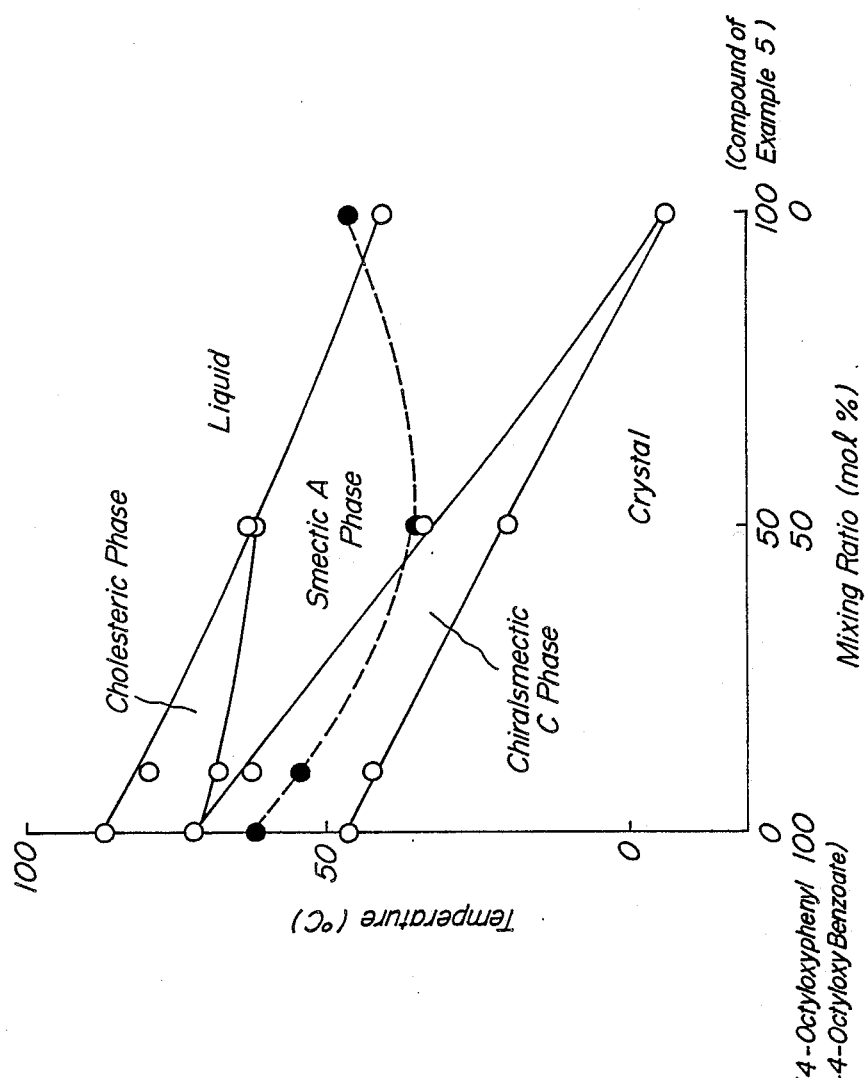
FIG. 1 is a phase diagram when 4-octyloxycarbonyloxy-4'-(2-methylbutanoyl) biphenyl obtained in Example 5 is mixed with a well-known compound of 4-octyloxyphenyl-4-octyloxy benzoate at various mixing ratios.

In the above general formula (I), the alkyl group shown by R and the integer of n are not particularly critical, but it is preferable that R has a carbon number of up to 18 and n is up to 16 from a viewpoint of actual production factors such as easy availability of starting materials and the like.

Moreover, carbon bonding $C_mH_{2m+1}$ in the above formula is an asymmetric carbon and, when an optical activity is introduced into the compound taking this carbon as an asymmetric center, the resulting optically active compound forms a ferroelectric liquid crystal having a fast response rate alone or in admixture with another compound.

Examples of the novel compounds shown by the formula (I) and their physical and chemical properties are as follows:

4-hexanoyloxy-4'-(2-methylbutanoyl) biphenyl

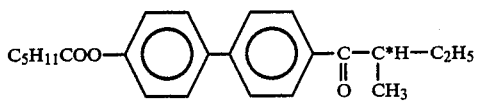

IR (KBR, cm$^{-1}$); 2910, 2840, 1745, 1675, 1600, 1225, 1190.
$^1$H-NMR (90 MHz): δ0.85–1.12 6H(m),
δ1.22 3H(d, J=7 Hz),
δ1.20–2.0 8H(m),
δ2.59 2H(t, J=7 Hz),
δ3.42 1H(m),
δ7.19 2H(d, J=9 Hz),
δ7.62 2H(d, J=9 Hz),
δ7.65 2H(d, J=9 Hz),
δ8.02 2H(d, J=9 Hz).

4-nonanoyloxy-4'-(2-methylbutanoyl) biphenyl

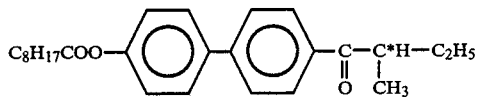

IR (KBr, cm$^{-1}$): 2910, 2840, 1745, 1675, 1600, 1230, 1190, 1150.
$^1$H-NMR (90 MHz): δ0.91 6H(m),
δ1.20 3H(d, J=7 Hz),
δ1.0–2.0 14H(m),
δ3.42 1H(m),
δ7.19 2H(d, J=9 Hz),
δ7.64 2H(d, J=9 Hz),
δ7.67 2H(d, J=9 Hz),
δ8.02 2H(d, J=9 Hz).

4-tetradecanoyloxy-4'-(2-methylbutanoyl) biphenyl

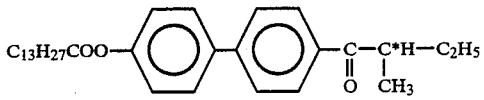

IR (KBr, cm$^{-1}$): 2910, 2840, 1745, 1675, 1600, 1225, 1190, 1145.
$^1$H-NMR (90 MHz): δ0.87–1.03 6H(m),
δ1.20 3H(d, J=7 Hz),
δ1.2–2.0 24H(m),
δ2.59 2H(t, J=7 Hz),
δ3.42 1H(m),
δ7.22 2H(d, J=9 Hz),
δ7.61 2H(d, J=9 Hz),
δ7.65 2H(d, J=9 Hz),
δ8.05 2H(d, J=9 Hz).

4-nonanoyloxy-4'-(2-methyloctanoyl) biphenyl

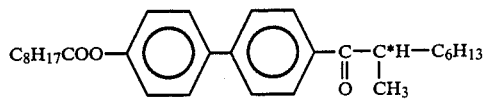

IR (KBr, cm$^{-1}$): 2910, 2840, 1755, 1675, 1462, 1375, 1200, 1140, 975, 827
$^1$H-NMR (90 MHz): δ0.90 6H(m),
δ1.21 3H(d, J=6.5 Hz),
δ1.2–2.0 22H(m),
δ2.58 2H(t, J=7 Hz),
δ3.48 1H(m),
δ7.16 2H(d, J=8.5 Hz),
δ7.60 2H(d, J=8.5 Hz),
δ7.62 2H(d, J=8 Hz),
δ7.99 2H(d, J=8 Hz), 4-octyloxycarbonyloxy-4'-(2-methylbutanoyl) biphenyl

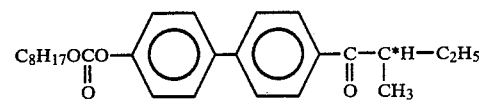

IR (KBr, cm$^{-1}$): 2910, 2840, 1750, 1675, 1600, 1275, 1220, 1185.
$^1$H-NMR (90 MHz): δ0.94 6H(m),
δ1.22 3H(d, J=7 Hz),
δ1.2–2.0 14H(m),
δ3.42 1H(m),
δ4.28 2H(t, J=7 Hz),
δ7.28 2H(d, J=9 Hz),
δ7.62 2H(d, J=9 Hz),
δ7.64 2H(d, J=9 Hz),
δ8.09 2H(d, J=9 Hz).

4-octyloxycarbonyloxy-4'-(2-methloctanoyl) biphenyl

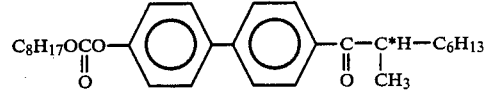

IR KBr, cm$^{-1}$): 2910, 2840, 1755, 1675, 1600, 1460, 1260, 1220, 972, 950, 820.
$^1$H-NMR (90MHz): δ0.89 6H(m),
δ1.23 3H(d, J=7 Hz),
δ1.2–2.0 22H(m),
δ3.49 1H(m),
δ4.28 2H(t, J=6 Hz),
δ7.27 2H(d, J=9 Hz),
δ7.62 4H(d, J=9 Hz),
δ8.01 2H(d, J=9 Hz), 4-nonanoyl-4'-(2-methyloctanoyl) biphenyl

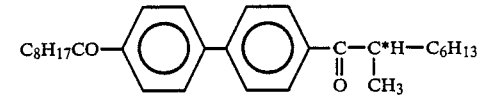

IR (KBr, cm$^{-1}$): 2910, 2840, 1680, 1600, 1480, 1372, 820.

$^1$H-NMR (90 MHz): δ0.88 6H(m),
δ1.21 3H(d, J=7 Hz),
δ1.2–2.1 22H(m),
δ3.00 2H(t, J=7 Hz)
δ7.69 4H(d, J=8 Hz),
δ8.05 4H(d, J=8 Hz),

Moreover, the length of the carbon chain of the alkyl group R shown by the formula (I) can properly be selected in accordance with the use purpose because the compound affects the temperature region forming a liquid crystal state. Of course, such compounds may be used alone or in admixture with the other liquid crystal material.

At first, compounds in which A in the formula (I) is a single bond are obtained by reacting 2-alkyl-1-alkanoic acid represented by the following general formula (1):

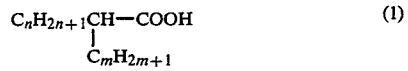

(wherein m and n are the same as mentioned above) with an inorganic halogen compound such as thionyl chloride, phosphorus pentachloride, phosphorus trichloride, phosphoryl chloride or the like to form an acyl halide, and then reacting the acyl halide with 4-alkyl-biphenyl in the presence of a catalyst such as anhydrous aluminum chloride, boron trifluoride or the like according the Friedel-Crafts reaction.

Moreover, 4-alkyl-biphenyl is obtained by acylating biphenyl with an alkyl carboxylic acid according to the Friedel-Crafts reaction to reduce a carbonyl group thereof to a methylene group. Alternatively, commercially available 4-alkyl-biphenyl may be used.

In order to obtain 2-alkylalkanoic acid of the general formula (1), 2-alkyl-1-alkanol represented by the following general formula (2):

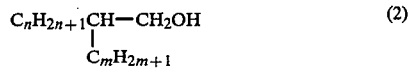

(wherein m and n are the same as mentioned above) is compound having an optical activity, 2-alkyl-1-alkanol having an optical activity may be used. In the latter case, an oxidizing agent capable of conducting oxidation without racemization is selected. Such an oxidation is most convenient to be carried out by using potassium permanganate under an acidic condition.

Secondly, compounds in which A of the general formula (I) is —COO— or —OCOO— are obtained as follows.

At first, 2-alkylalkanoic acid of the above formula (1) is esterified with hydroxy biphenyl by condensation. This esterification easily proceeds at a temperature of 60°~120° C. in the presence of a mineral acid catalyst. In this case, it is favorable to carry out the reaction in the presence of an organic solvent such as benzene, toluene, xylene or the like under reflux. As the mineral acid catalyst, use may be made of hydrochloric acid, sulfuric acid, thionyl chloride, boron fluoride and so on.

Then, biphenyl-2-alkylalkanoate is reacted with a 2-alkylalkanoyl halide. That is, when biphenyl-2-alkylalkanoate and the halide are reacted in the presence of a catalyst such as anhydrous aluminum chloride, boron trifluoride or the like, 2-alkylalkanoyl is added to 4'-position of the above biphenyl ester to produce 4'-(2-alkylalkanoyl) biphenyl-2-alkylalkanoate without racemization when 2-alkylalkanoyl halide has an optical activity. In this case, 2-alkylalkanoic acid may be the same as 2-alkylalkanoic acid used in the above esterification, or another compound having a different chain length may naturally be used.

This reaction operation may be carried out by dissolving the above biphenyl-2-alkylalkanoate and 2-alkylalkanoyl halide in an organic solvent such as nitrobenzene, dichloromethane or the like, maintaining temperature at −20° C.~50° C. and stirring for 1–100 hours.

The resulting 4'-(2-alkylalkanoyl) biphenyl-2-alkylalkanoate is hydrolyzed with an alkali such as sodium hydrogen carbonate, potassium hydrogen carbonate or the like in the presence of a solvent such as alcohol/water or the like, and then neutralized with an inorganic acid such as hydrochloric acid, sulfuric acid or the like to obtain 4-hydroxy-4'-(2-alkylalkanoyl) biphenyl represented by the following general formula (3):

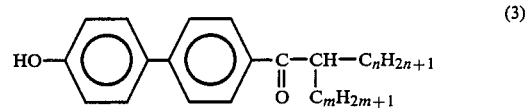

ps (wherein m and n are the same as mentioned above).

The compounds in which A of the formula (I) is —COO— are obtained by esterifying the above compound (3) with an alkanoic acid or a halide thereof, while the compounds in which A is —OCOO— are obtained by reacting the above compound (3) with an alkyl chloroformate.

Thirdly, compounds in which A of the formula (I) is —OCO— are obtained as follows.

At first, commercially available 4-halobiphenyl and acetyl chloride are reacted to form 4-acetyl-4'-halobiphenyl, which is converted into 4'-halobiphenyl-4-carboxylic acid according to a haloform reaction and reduced with lithium aluminum hydride to form 4'-halo-4-hydroxymethyl biphenyl. This compound is reacted with an alkylvinyl ether to form 4-(4-halophenyl) benzyl-(1-alkoxy) ethylether, which is coupled with 2-alkylalkanoyl chloride according to Grignard's reaction and a protective group is removed therefrom under an acidic condition to obtain 4'-(2-alkylalkanoyl)-4-hydroxymethyl biphenyl represented by the following general formula (4):

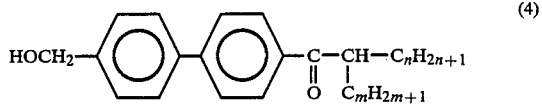

(wherein m and n are the same as mentioned above) without racemization in the case of compounds having an optical activity.

Then, the above 4'-(2-alkylalkanoyl)-4-hydroxymethyl biphenyl is oxidized with an oxidizing agent such as potassium permanganate or the like to obtain 4'-(2-alkylalkanoyl) biphenyl-4-carboxylic acid represented by the following general formula (5):

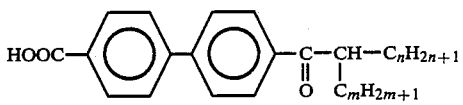

(wherein m and n are the same as mentioned above) without racemization in case of compounds having an optical activity.

Thereafter, the above compound (5) is esterified with an alkanol to obtain the compound in which A of the formula (I) is —OCO—.

Fourthly, compounds in which A of the formula (I) is —CO— are obtained as follows.

At first, a 2-alkylalkanoyl halide of the formula (1) is reacted with biphenyl. That is, when biphenyl and the halide are reacted in the presence of a catalyst such as anhydrous aluminum chloride, boron trifluoride or the like, 2-alkylalkanoyl is added to the 4-postion of biphenyl without racemization when 2-alkylalkanoyl halide has a optical activity to produce 4-(2-alkylalkanoyl) biphenyl.

Then, the above 4-(2-alkylalkanoyl) biphenyl is reacted with an acyl complex of alkanoyl halide and aluminum chloride or the like to obtain 4-alkanoyl-4'-(2-alkylalkanoyl) biphenyl.

Moreover, it is a matter of course that the order of acylations of 2-alkylalkanoic acid and alkanoic acid may be changed in the above reactions.

The compounds according to the invention can have a stable thermotropic liquid crystal state and form ferroelectric liquid crystals having a large spontaneous polarization and a fast response rate, so that they develop a very excellent effect as a material for optoelectronics and their related elements.

Therefore, it can be said that the compounds according to the invention are liquid crystal materials suitable for optoelectronics and their related elements utilizing liquid crystal properties or electro-chemichromism, for example, a display for liquid crystal television receiver, optical printer head, opto-Fourier transform element, light valve and the like.

The following examples are given in illustration of the invention and are not intended as limitations thereof.

EXAMPLE 1

4-hexanoyloxy-4'-(2-methylbutanoyl) biphenyl

Synthesis of (+)-4-hydroxy-4'-(2-methylbutanoyl) biphenyl

Into a flask were charged 1800 ml of water and 255 g of sulfuric acid, to which were suspended 100 g (1.13 mol) of (−)-2-methyl butanol. Thereafter, 278 g (1.76 mol) of potassium permanganate were added thereto over 3 hours while maintaining at 23°~25° C., and further reacted at this temperature. After the completion of the reaction, the reaction solution was placed in a vessel containing 1 l of ice water, added with 220 g (2.11 mol) of sodium bisulfite and further with 30 ml of concentrated sulfuric acid to adjust the pH to not more than 1, and extracted with diethyl ether. The extract was extracted with a 10% aqueous solution of sodium hydroxide, which was then added with 200 ml of water and 370 ml of concentrated hydrochloric acid to adjust the pH to not more than 1. After the aqueous solution was extracted with dichloromethane, the extract was dried on anhydrous magnesium sulfate. The dried extract was concentrated and distilled under a reduced pressure (59.5°~60° C./4~5 mmHg) to obtain 78.0 g (yield: 68%) of a transparent liquid of (+)-2-methyl butanoic acid.

Then, 5.49 g of the above (+)-2-methyl butanoic acid, 8.50 g of 4-hydroxybiphenyl and 20 ml of toluene were charged into a flask, and added with 4.0 ml of thionyl chloride with stirring, which was reacted for 8 hours while maintaining the temperature at 70°~80° C. After completion of the reaction, the reaction solution was cooled to room temperature, added with water to decompose excess thionyl chloride, washed with water, and dried on anhydrous magnesium sulfate. After the solvent was distilled off, the residue was purified through a column chromatography of silica gel to obtain 12.69 g of oily (+)-bphenyl-2-methylbutanoate having a specific rotary power $[\alpha]^{25}_D +15.1°$ (11.03% by weight in chloroform).

In a flask was charged 11.7 g (98.3 mmol) of thionyl chloride and was maintained at 36°~38° C., to which was added dropwise 8.98 g (87.3 mmol) of the above (+)-2-methylbutanoic acid over 7 minutes with stirring. After stirring and reacting at room temperature for 40 minutes, the reaction mixture was further reacted by stirring at a temperature of 80° C. for 30 minutes. Then, it was distilled to obtain 6.5 g (53. 9 mmol, yield: 64%) of a colorless and transparent (+)-2-methyl butanoyl chloride.

Then, 4.0 g of (+)-2-methyl butanoyl chloride and 7 ml of nitrobenzene were charged into a flask and cooled to 0° C., added with 10.74 g (80 mmol) of anhydrous aluminum chloride and further with a solution of 4.97 g (19.6 mmol) of (+)-biphenyl-2-methylbutanoate in 9 ml of nitrobenzene, which was stirred at room temperature for 70 hours. After the addition of 2 normal hydrochloric acid and ice, the extraction with chloroform was performed. The extracted chloroform phase was washed with water, dried on anhydrous magnesium sulfate, and the solvent was distilled off. The residue was purified through a column chromatography of silica gel after distillation off of the solvent to obtain 3.60 g (yield: 54%) of an oily (+)-4-(2-methylbutanoyl) biphenyl-2-methylbutanoate. The NMR analytical values of this product were as follows.

$^1$H-NMR (in CDCl$_3$, TMS standard, ppm): 8.02(d, 2H), 7.63(d, 2H), 7.60(d, 2H), 7.20(d, 2H), 3.42(m, 1H), 2.67(m, 1H), 1.75–1.95(m, 2H), 1.4–1.75(m, 2H), 1.32(d, 3H), 1.20(d, 3H), 1.06(t, 3H), 0.96(t, 3H)

To a mixture of 0.67 g of the above (+)-4-(2-methylbutanoyl) biphenyl-2-methylbutanoate, 95 ml of methanol and 5 ml of water was added 1.14 g (13.6 mmol) of sodium hydrogen carbonate with stirring, which was subjected to a hydrolysis reaction at room temperature for 40 hours. After completion of the reaction, methanol was distilled off, and the residue was added with 1 normal hydrochloric acid to adjust the pH to not more than 1 and extracted with dichloromethane. The extract was washed with water, dried on anhydrous magnesium sulfate and the solvent was distilled off. The residue was purified through a column chromatography of silica gel after the distillation off of the solvent to obtain 0.44 g (yield: 88%) of a light yellow crystal of (+)-4-hydroxy-4'-(2-methybutanoyl) biphenyl.

① $^1$H-NMR (in CDCl$_3$, TMS standard, ppm): 8.05(d, 2H), 7.65(d, 2H), 7.53(d, 2H), 7.06(d, 2H), 3.50(m, 1H), 2.10–1.40(m, 2H), 1.22(d, 3H), 0.96(t, 3H), ② IR (KBr, cm$^{-1}$): 3300, 2930, 2910, 1650, 1590.

③ Mass: 254(M+).
④ $[\alpha]^{25}_D$(8.6% by weight, in CDCl$_3$): + 19.0°

Synthesis of 4-hexanoyloxy-4'-(2-methylbutanoyl) biphenyl

Into a flask were charged 240.4 mg (0.95 mmol) of 4-hyroxy-4'-(2-methylbutanoyl) biphenyl, 0.15 g (1.29 mmol) of hexanoic acid, 0.24 g (1.17 mmol) of dicyclohexyl carbodiimide, 10 mg (0.08 mmol) of 4-dimethylamino pyridine and 7 ml of dried dichloromethane, which were stirred at room temperature for 1 hour. After the resulting solid was filtered off and the solvent was distilled off, the residue was purified through a column chromatography of silica gel and recrystallized from ethanol to obtain 25.5 mg (yield: 8%) of a white crystal of 4-hexanoyloxy-4'-(2-methylbutanoyl) biphenyl.

Evaluation of liquid crystal properties

After the above compound was placed in a 4 μm thick cell having ITO deposited glass plates with rubbed polyimide films, the temperature of the cell was controlled on a hot stage, during which the state of the compound in the cell was observed under crossed Nicols. When the change of the compound was observed by varying the temperature in the hot stage at a rate of 2° C./min, it changed from an isotropic liquid to smectic A phase at 57° C., a highly ordered liquid crystal phase at 32° C. and another highly ordered liquid crystal phase at 15° C., and was crystallized at −27° C. during the cooling.

EXAMPLE 2

4-nonanoyloxy-4'-(2-methylbutanoyl) biphenyl

Synthesis of 4-nonanoyloxy-4'-(2-methylbutanoyl) biphenyl

Into a flask were charged 247.7 mg (0.98 mmol) of 4-hydroxy-4'-(2-methylbutanoyl) biphenyl obtained in the same manner as in Example 1, 10 ml of dried pyridine and 0.5 ml (2.50 mmol) of nonanoyl chloride, which was stirred at room temperature for 4.5 hours. Thereafter, a saturated aqueous solution of sodium hydrogen carbonate was added and extraction with ether was carried out three times. The extracted organic layers were combined and washed with a saturated aqueous solution of sodium chloride. Then, it was dried on anhydrous magnesium sulfate and the solvent was distilled off. The residue was purified through a column chromatography of silica gel and recrystallized from ethanol to obtain 160.4 mg (yield: 42%) of a white crystal of 4-nonanoyloxy-4'-(2-methylbutanoyl) biphenyl.

Evaluation of liquid crystal properties

When the above compound was observed by the same method as in Example 1, it changed from an isotropic liquid into smectic A phase at 65.1° C. and was crystallized at 40° C. during the cooling. Further, it changed from the crystal into smectic A phase at 47.8° C. during heating.

EXAMPLE 3

Synthesis of 4-tetradecanoyloxy-4'-(2-methylbutanoyl) biphenyl

Into a flask were charged 229.0 mg (0.90 mmol) of 4-hydroxy-4'-(2-methylbutanoyl) biphenyl obtained in the same manner as in Example 1, 0.5 ml (1.82 mmol) of tetradecanoyl chloride and 6 ml of dried pyridine, which was stirred at room temperature for 4 hours. Then, a saturated aqueous solution of sodium hydrogen carbonate was added, and the extraction with ether was carried out three times. Thereafter, the extracts were dried on anhydrous magnesium sulfate and the solvent was distilled off. The residue was purified through a column chromatography of silica gel and recrystallized from ethanol to obtain 292.5 mg (yield: 70%) of a white crystal of 4-tetradecanoyloxy-4'-(2-methylbutanoyl) biphenyl.

Evaluation of liquid crystal properties

When the above compound was observed by the same method as in Example 1, it changed from an isotropic liquid into smectic A phase at 66.7° C. and was crystallized at 62° C. during cooling. Further, it changed from the crystal into an isotropic liquid at 69.4° C. during heating.

EXAMPLE 4

4-nonanoyloxy-4'-(2-methyloctanoyl) biphenyl

Synthesis of (+)-4-hydroxy-4'-(2-methyloctanoyl) biphenyl

To 21.2 g (147 mmol) of (−)-2-methyloctanol were added an aqueous solution of 330 ml of water and 46.4 g of concentrated sulfuric acid, which was stirred to form an emulsion. To this emulsion was added dropwise 63.4 g (401 mmol) of potassium permaganate over 7 hours. Then, the reaction mixture was added with 51.5 g of sodium bisulfite and poured into 270 ml of ice water together with 70 ml of ice water and 200 ml of ether. After the separation into two layers, the reaction product was extracted from the aqueous layer with ether, which was further extracted with a 10% aqueous solution of sodium hydroxide, added with ice and further with a concentrated hydrochloric acid to adjust the pH to not more than 1. Thereafter, the extraction with chloroform on the aqueous layer was performed, which was washed with water, dried on magnesium sulfate and filtered. The filtrate was concentrated and distilled under a reduced pressure to obtain 16.5 g (yield: 71%) of a colorless and transparent liquid of (+)-2-methyl octanoic acid.

Then, 2.02 g (12.8 mmol) of the above (+)-2-methyl octanoic acid, 2.02 g (11.9 mmol) of 4-hydroxy biphenyl and 10 ml of toluene were charged into a flask, and further 1.0 ml (13.7 mmol) of thionyl chloride was added with stirring, which were then reacted for 9 hours while maintaining at a temperature of 70°~80° C. After the completion of the reaction, the reaction mixture was cooled to room temperature, added with water to decompose excess thionyl chloride, washed with water and then dried on anhydrous magnesium sulfate. After the solvent was distilled off, the residue was purified through a column chromatography of silica gel to obtain 3.43 g of an oily (+)-biphenyl-2-methyloctanoate having a specific rotary power $[\alpha]^{25}_D = +16.3°$ (2.6% by weight, in chloroform).

Then, 2.38 g (19.0 mmol) of thionyl chloride was maintained at a temperature of 36°~38° C. in a flask, to which was added dropwise 2.51 g (15.9 mmol) of the above (+)-2-methyl octanoic acid over 7 minutes with stirring. After the reaction with stirring at room temperature for 40 minutes, the reaction was further continued by stirring at a temperature of 80° C. for 30 minutes. Then, the reaction product was distilled to obtain 2.81 g (15.9 mmol, yield: 100%) of a colorless and transparent (+)-2-methyl octanoyl chloride.

Next, 2.02 g (11.4 mmol) of the above (+)-2-methyl octanoyl chloride and 3 ml of nitrobenzene were cooled to 0° C. in a flask and added with 3.06 g (22.9 mmol) of anhydrous aluminum chloride with stirring, which were stirred at room temperature for 30 minutes. Thereafter, 2.89 g (7 mmol) of (+)-biphenyl-2-methyloctanoate biphenyl dissolved in 3 ml of nitrobenzene was added thereto, which was reacted by stirring at room temperature for 140 hours. After the completion of the reaction, 2 normal hydrochloric acid and ice were added and extracted with chloroform. The extract was washed with water, dried on anhydrous magnesium sulfate and distilled to remove the solvent. The residue was purified through a column chromatography of silica gel to obtain 1.55 g (yield: 49%) of an oily (+)-4-(2-methyloctanoyl) biphenyl-2-methyloctanoate.

Into a flask were charged 0.85 g (1.9 mmol) of the above (+)-4-(2-methyloctanoyl) biphenyl-2-methyloctanoate, 70 ml of methanol and 5 ml of water, and 0.98 g (11.7 mmol) of sodium hydrogen carbonate was added with stirring, which were then reacted at room temperature for 46 hours. After the completion of the reaction, methanol was distilled off, and the residue was added with 1 normal hydrochloric acid to adjust the pH to not more than 1 and extracted with dichloromethane. The extract was washed with water, dried on anhydrous magnesium sulfate, distilled to remove the solvent and purified through a column chromatography of silica gel to obtain 0.54 g (yield: 92%) of a light yellow crystal of (+)-4-hyroxy-4'-(2-methyloctanoyl) biphenyl having the following physical and chemical properties:

① $^1$H-NMR (in CDCl$_3$, TMS standard, ppm): 7.98(d, 2H), 7.60(d, 2H), 7.50(d, 2H), 6.92(d, 2H), 6.00(br, 1H), 3.84(m, 1H), 2.00-1.15(m, $_0$H), 1.22(d, 3H), 1.0-0.75(m, 3H).

② IR (neat, cm$^{-1}$): 3300, 2900, 2850, 1650, 1585

③ Mass: 310(M+).

④ $[\alpha]^{25}{}_D$(3.2% by weight, in CHCl$_3$): + 6.2°

Synthesis of 4-nonaoyloxy-4'-(2-methyloctanoyl) biphenyl

Into a flask of were charged 130.0 mg (0.42 mmol) of the above 4-hydroxy-4'-(2-methyloctanoyl) biphenyl, 5 ml of dried pyridine and 0.3 ml of nonanoyl chloride, which were stirred at room temperature for 40 hours. Then, a saturated aqueous solution of sodium hydrogen carbonate was added, and the extraction with ether was carried out three times. Thereafter, the extract was dried on magnesium sulfate and the solvent was distilled off. The residue was purified through a column chromatography of silica gel and recrystallized from ethanol to obtain 77.1 mg (yield: 41%) of a white crystal of 4-nonanoyloxy-4'-(2-methyloctanoyl) biphenyl.

Evaluation of liquid crystal properties

When the above compound was observed by the same method as in Example 1, it changed from an isotropic liquid into a crystal at 45.8° C. during the cooling. Further, it changed from the crystal into the isotropic liquid at 50.6° C. during the heating.

EXAMPLE 5

4-octyloxycarbonyloxy-4'-(2-methylbutanoyl) biphenyl

Synthesis of 4-octyloxycarbonyloxy-4'-(2-methylbutanoyl) biphenyl

Into a flask were charged 210.1 mg (0.83 mmol) of 4-hydroxy-4'-(2-methylbutanoyl) biphenyl, 5 ml of dried pyridine and 0.5 ml (2.34 mmol) of octyl chloroformate, which were then stirred at room temperature for 2 hours. Then, a saturated aqueous solution of sodium hydrogen carbonate was added, and the extraction with ether was carried out three times. Thereafter, the extract was dried on anhydrous magnesium sulfate and distilled to remove the solvent. The residue was purified through a column chromatography of silica gel and recrystallized from ethanol to obtain 04.7 mg (yield: 60%) of a white crystal of 4-octyloxycarbonyloxy-4'-(2-methylbutanoyl) biphenyl.

Evaluation of liquid crystal properties

When the above compound was observed by the same method as in Example 1, it changed from an isotropic liquid into a smectic A phase at 41.6° C. and was crystallized at −6.3° C. during the cooling. Further, it changed from the crystal into the isotropic liquid at 47.3° C. during the heating.

EXAMPLE 6

4-octyloxycarbonyloxy-4'-(2-methyloctanoyl) biphenyl

Synthesis of 4-octyloxycarbonyloxy-4'-(2-methyloctanoyl) biphenyl

Into a flask were charged 132.0 mg (0.43 mmol) of 4-hydroxy-4'-(2-methyloctanoyl) biphenyl obtained in the same manner as in Example 4, 3 ml of dried pyridine and 0.2 ml (1.02 mmol) of octyl chloroformate, which were then stirred at room temperature for 2 hours. Then, a saturated aqueous solution of sodium hydrogen carbonate was added, and the extraction with ether was carried out three times. Then, the extract was dried on anhydrous magnesium sulfate and distilled to remove the solvent. The residue was purified through a column chromatography and recrystallized from ethanol to obtain 59.1 mg (yield: 30%) of a white crystal of 4-octyloxycarbonyloxy-4'-(2-methyloctanoyl) biphenyl.

Evaluation of liquid crystal properties

When the above compound was observed by the same method as in Example 1, it changed from an isotropic liquid into a crystal at 34.8° C. during cooling. Further, it changed from the crystal into the isotropic liquid at 48.6° C. during heating.

EXAMPLE 7

4-nonanoyl-4'-(2-methyloctanoyl) biphenyl

Synthesis

Into a flask were charged 1.00 g (5.67 mmol) of 2-methyloctanoyl chloride obtained in the same manner as in Example 4, 2 ml of dried nitrobenzene and 0.80 g (5.99 mmol) of anhydrous aluminum chloride, which were then stirred at room temperature for 10 minutes. Then, 0.90 g (5.84 mmol) of biphenyl was added thereto and further stirred at room temperature for 1 hour.

Separately, 2.00 g (11.33 mmol) of nonanoyl chloride and 1.60 g (11.98 mmol) of anhydrous aluminum chloride were charged into a flask and stirred at room temperature for 10 minutes to form an acyl-aluminum complex. The complex was added to the aforementioned flask, which was stirred at room temperature for 3 days and at 50° C. for 2 days. Thereafter, 1 normal hydrochloric acid was added, and the extraction with ether was carried out three times. The extracted organic layers were combined, washed with a saturated aqueous solution of sodium hydrogen carbonate two times and dried on anhydrous magnesium sulfate. After the solvent was distilled off, the residue was purified through a column chromatography of silica gel and recrystallized from ethanol to obtain 149.1 mg (yield: 6%) of a light yellow crystal of 4-nonanoyl-4'-(2-methyloctanoyl) biphenyl.

Evaluation of liquid crystal properties

When the above compound was observed by the same method as in Example 1, it changed from an isotropic liquid into a crystal at 133° C. during cooling.

EXAMPLE 8

Preparation of liquid crystal composition

There was prepared an equimolar mixture of 4-octyloxycarbonyloxy-4'-(2-methylbutanoyl) biphenyl obtained in Example 5 and 4-octyloxycarbonyloxy-4'-(2-methyloctanoyl) biphenyl obtained in Example 6. When the liquid crystal properties of this mixture were measured by the same method as in Example 1, the mixture changed from an isotropic liquid into smectic A phase at 28° C. and ferroelectric phase at −5° C. and was completely crystallized at −15° C. during cooling. Thus, the ferroelectric liquid crystal phase could be developed even at a fairly low temperature by mixing.

EXAMPLE 9

Preparation of liquid crystal composition 4-octyloxycarbonyloxy-4'-(2-methylbutanoyl) biphenyl obtained in Example 5 was mixed with a wellknown compound of 4-octyloxyphenyl-4-octyloxy benzoate having no ferroelectricity but exhibiting chiral smectic C phase at various mixing ratios to prepare a phase diagram, which was shown in FIG. 1. In FIG. 1, the abscissa shows a mol ratio of the compound mixed, and the ordinate shows a phase transformation temperature, and also mark ○ shows a phase transformation temperature during cooling and mark ● shows a temperature of fusing the crystal during heating.

As seen from FIG. 1, the liquid crystal composition exhibiting a chiral smectic C phase at about room temperature was prepared by mixing about 50 mol% of 4-octyloxycarbonyloxy-4'-(2-methylbutanoyl) biphenyl.

For comparison, FIG. 2 shows a phase diagram when the aforementioned 4-octyloxy-4'-(2-methylbutanoyl) biphenyl obtained by replacing the connecting group between alkyl chain and biphenyl in 4-octyloxycarbonyloxy-4'-(2-methylbutanoyl) biphenyl (Japanese Patent laid open No. 60-13729) was mixed with 4-octyloxyphenyl-4-octyloxy benzoate at various mixing ratios. In FIG. 2, the abscissa, ordinate, mark ○ and mark ● are the same as in FIG. 1.

In this case, it is understood that the chiral smectic C phase is not exhibited when mixing with 50 mol% of 4-octyloxy-4'-(2-methylbutanoyl) biphenyl. Therefore, it can be seen that the compounds according to the invention form a preferable liquid crystal composition having a more stable chiral smectic C phase.

EXAMPLE 10

Manufacture of light switching element

A liquid crystal composition obtained by mixing 50 mol% of 4-octyloxycarbonyloxy-4'-(2-methylbutanoyl) biphenyl obtained in Example 9 with 50 mol% of 4-octyloxyphenyl-4-octyloxy benzoate was placed in a 5 $\mu$m thick cell having ITO deposited glass plates with rubbed polyimide films, and then gently cooled from a state of an isotropic liquid to orient into a smectic A phase. Further, the state was changed into a chiral smectic C phase by lowering the temperature, during which when electric field was applied to the cell while observing under crossed Nicols, clear switching operation was observed.

When a rectangular wave of 66 Vpp was applied at 24° C. to the cell and a light transmitted quantity was measured by means of a photodiode to detect the switching operation, the response time was 31 $\mu$sec.

What is claimed is:

1. A novel biphenyl compound represented by the following general formula (I):

$$R-A-\underset{}{\bigcirc}-\underset{}{\bigcirc}-\underset{\underset{O}{\overset{\|}{C}}}{\overset{}{-}}-\underset{\underset{C_mH_{2m+1}}{|}}{\overset{}{CH}}-C_nH_{2n+1} \quad (I)$$

wherein R is an alkyl group, A is selected from a single bond, —COO— and —OCOO— and each of m and n is an integer of 1 or more provided m<n.

2. The biphenyl compound of claim 1, wherein a value of m in the general formula (I) is 1.

3. The biphenyl compound of claim 1 wherein said compound of the general formula (I) is an optically active compound.

4. A liquid crystal composition containing at least one of biphenyl compounds represented by the general formula (I) as claimed in claim 1.

5. A light switching element comprising at least one of biphenyl compounds represented by the general formula (I) as claimed in claim 1.

* * * * *